United States Patent [19]

Nguyen et al.

[11] Patent Number: 5,736,530
[45] Date of Patent: Apr. 7, 1998

[54] GUANYLIC ACID DERIVATIVES AND THEIR USE AS DRUGS

[75] Inventors: Dat Xuong Nguyen, Antony; Jean Rapin, Paris; Patrick Lambropoulos, Marseilles; Jean Daver, Saix, all of France

[73] Assignee: Societe de Recherche Auvergnate pour l'Innovation en Oligotherapie-Inoligo-, Chamalieres, France

[21] Appl. No.: 750,477

[22] PCT Filed: Jun. 16, 1995

[86] PCT No.: PCT/FR95/00806

§ 371 Date: Jan. 29, 1997

§ 102(e) Date: Jan. 29, 1997

[87] PCT Pub. No.: WO95/35305

PCT Pub. Date: Dec. 28, 1995

[30] Foreign Application Priority Data

Jun. 17, 1994 [FR] France .................... 94 07490

[51] Int. Cl.$^6$ .................... A61K 31/70; C07H 19/167
[52] U.S. Cl. .................... 514/48; 536/27.81
[58] Field of Search .................... 514/48; 536/27.81

[56] References Cited

U.S. PATENT DOCUMENTS 2,058,180  10/1936  Ruskin .................... 536/27.81
3,557,081  1/1971  Suzuki et al. .................... 536/27.81

OTHER PUBLICATIONS

Chem. Abst. 105:201988, Campomar et al., 1986.
Chem. Abst. 103:123845, Sekine et al., 1985.
Chem. Abst. 99:176208, Kamimura et al., 1983.

*Primary Examiner*—Raymond Henley, III
*Attorney, Agent, or Firm*—Oblon, Spivak, McClelland, Maier & Neustadt, P.C.

[57] ABSTRACT

Guanylic acid derivatives according to either of the formulae:

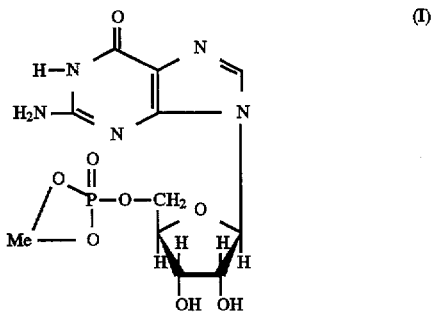

(I)

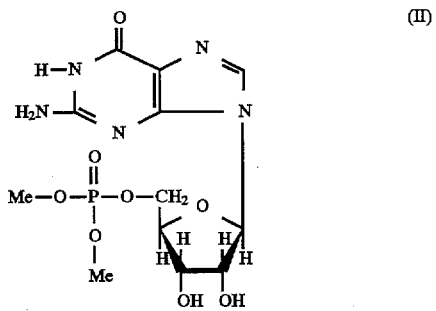

(II)

in which Me is a metal trace element indispensable for the enzymatic activity of physiological processes.

These derivatives, prepared in gastro-resistant galenic form with in situ release of active ingredients, are proposed for the treatment of psychasthenia, depression, anxiety and geriatric disorders.

10 Claims, No Drawings

GUANYLIC ACID DERIVATIVES AND THEIR USE AS DRUGS

This is a 371 of PCT/FR95/00806 filed Jun. 16, 1995.

The present invention relates to guanylic acid derivatives and the use of these substances as drugs.

The molecule of 5'-guanylic acid and the processes for obtaining this molecule have already been described in the literature. In particular reference is made to this product in the Merck Index, 11$^{th}$ edition (Reference N° 4484). It is known that this molecule in the form of a sodium salt may be used as a flavouring.

Also, this molecule has an important physiological role. Guanylic acid is a precursor of cyclic GMP which plays a known part in micro-circulation.

A physiological balance exists both between adenosine and guanosine and between the two cations calcium and magnesium. The excess of intracellular calcium and adenosine observed in elderly people leads to slowing of intellectual activity and asthenia. Magnesium and guanosine appear to have a reverse effect.

The therapeutic action, however, of the derivatives of guanylic acid have not, to the knowledge of the applicant, ever been described.

There is however a considerable, increasing need for an effective drug without side effects to treat biological disorders related to ageing.

The applicant has set out to research molecules that meet this need, and has thus been able to show that derivatives of guanylic acid can be used, among other uses, to treat these disorders and that they are non toxic.

The present invention relates to derivatives of guanylic acid according to either of the general formulae (I) and (II) in which Me is a metal trace element involved in the enzymatic activity of physiological processes, such as calcium (Ca), magnesium (Mg), copper (Cu), cobalt (Co), nickel (Ni), zinc (Zn), iron (Fe), selenium (Se), lithium (l), manganese (Mn) or any other monovalent or divalent cation chelated by guanylic acid:

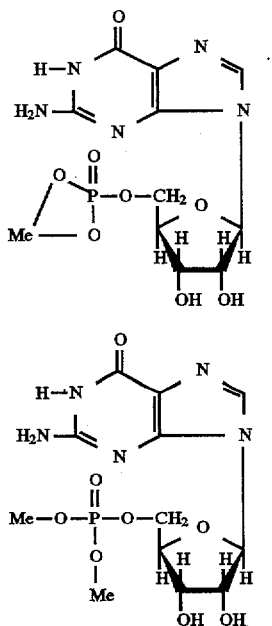

It will be noted that in formula II the two metal substituants on the derivative may be different.

These derivatives are advantageously in the form of a microcrystalline powder that is insoluble in water. They may be used alone or in association in formulations or compositions suitable for therapeutic use.

Such compositions are preferably gastro-resistant in order to prevent hydrochloric acidity of the stomach acting on the derivatives of the invention. Such compositions may be those which comply with the standards of the French Pharmacopeia.

The derivatives may be in the form of racemic mixtures or in the form of stereo-isomers.

The present invention also relates to the hydrated forms of the above-described derivatives, in particular those in which 6 to 8 water molecules are complexed.

As a general rule, in particular at neutral pH, the derivatives of the invention are in the form of non-ionized complexes. At acid pH such complexes are likely to break up and form ionized derivatives.

The derivatives of the present invention may be prepared by solubilizing guanylic acid in a nonpolar organic solvent and adding the cation in the form of a chloride. The reaction is stoichiometric with a yield in the region of 100%. A change in colour indicates the formation of the derivatives. After eliminating the solvents, the microcrystalline powders are washed in water to eliminate the traces of cation which are unreacted. After drying, the powder has a microcrystalline form and is insoluble in water and polar solvents. The melting point of all compounds is in the region of 300° C. The NMR spectrum, centesimal analysis and a single spot in thin layer chromatography confirm the structure and the purity of the derivatives obtained. Spectral X-ray analysis demonstrates that these derivatives are chelates.

The invention also relates to pharmaceutical compositions comprising at least one derivative such as described above, in conjunction with one or more diluent carriers, either excipients or additives that are compatible and pharmaceutically acceptable.

The pharmaceutical compositions of the invention are preferably in an appropriate form for administration through oral, parenteral or intravenous route.

Advantageously the pharmaceutical compositions of the invention contain a quantity of derivative as described above, adapted to a daily dosage in man of between approximately 0.2 g and approximately 3 g in one or several doses.

The invention relates more particularly to a composition or medicinal product containing a derivative such as described above and the use of such derivative in order to obtain medicinal products intended to treat:

cerebral asthenia, by stimulating cognitive functions such as the memory, psychasthenia, depression in mild and serious forms, anxiety, cation deficiency, such as those complexed in the compounds of the invention, vascular disorders relating to macro or micro circulation such as vasodilatation.

The derivatives that are the subject of this invention demonstrate in particular an anti-radical, healing, vasodilator effect.

In comparison with the molecules already used to treat the illnesses and disorders indicated above, the derivatives of the present invention have numerous advantages. In particular they are non toxic and have easy cell penetration properties. Moreover, they help cation entry into these cells via the specific channels.

The invention is illustrated by the following, non-limiting, examples:

EXAMPLE 1

Preparation of calcium 5'-guanylate or 5'-guanylicate

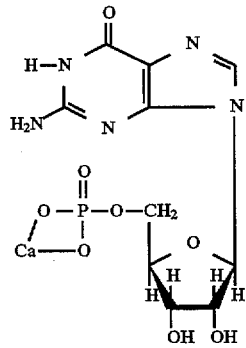

Molecular weight: 401 (anhydrous)
Centesimal composition:

| | |
|---|---|
| C % | 29.95 |
| H % | 3.02 |
| N % | 17.47 |
| Ca % | 10.04 |

Procedure 0.002 mole of 0.85 g of disodium 5'-guanylate (or 5'-guanylicate) (marketed by Fluka under reference 51090) are dissolved (warming slightly) in 10 ml of distilled water. 0.0025 mole of 95% calcium chloride or 0.25 g are dissolved separately in 10 ml of water. Under vigorous stirring the calcium solution is added to the sodium solution. A colourless precipitate is immediately formed and stirring is continued.

After dewatering the precipitate is washed with distilled water to eliminate the residual sodium chloride.

Recrystallisation is carried out in absolute ethanol (which does not dissolve the residual sodium chloride).

EXAMPLE 2

Preparation of magnesium 5'guanylate or 5'-granylicate

| | |
|---|---|
| Molecular formula: | $C_{10}H_{12}N_5O_8P.Mg$ (with n $H_2O$) |
| Molecular weight: | 385 (anhydrous) |
| Centesimal composition: | |
| C % | 31.19 |
| H % | 3.14 |
| N % | 18.19 |
| Mg % | 6.32 |

EXAMPLE 3

Preparation of manganese 5'guanylate or 5'-guanylicate

| | |
|---|---|
| Molecular formula: | $C_{10}H_{12}N_5O_8P.Mn$ (with n $H_2O$) |
| Molecular weight: | 415.93 or 416 (anhydrous) |
| Centesimal composition: | |
| C % | 28.85 |
| H % | 2.91 |
| N % | 16.84 |
| Mn % | 13.24 |

EXAMPLE 4

Preparation of copper (cuprous) 5'-guanylate or 5'-guanylicate

| | |
|---|---|
| Molecular formula: | $C_{10}H_{12}N_5O_8P.Cu$ (with n $H_2O$) |
| Molecular weight: | 424.50 (anhydrous) |
| Centesimal composition: | |
| C % | 28.29 |
| H % | 2.85 |
| N % | 16.50 |
| Cu % | 14.97 |

EXAMPLE 5

Preparation of iron (ferrous) 5'-guanylate or 5'-guanylicate

| | |
|---|---|
| Molecular formula: | $C_{10}H_{12}N_5O_8P.Fe$ (with n-$H_2O$) |
| Molecular weight: | 416.85 (anhydrous) |
| Centesimal composition: | |
| C % | 28.82 |
| H % | 2.90 |
| N % | 16.80 |
| Fe % | 13.48 |

EXAMPLE 6

Preparation of lithium 5'-guanylate or 5'-guanylicate

| | |
|---|---|
| Molecular formula: | $C_{10}H_{12}N_5O_8P.Li_2$ (with n $H_2O$) |
| Molecular weight: | 375 (anhydrous) |

Structural formula:

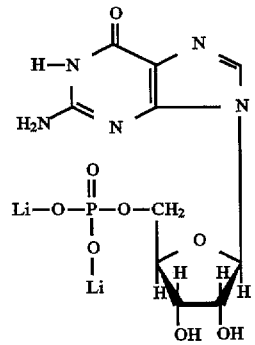

| Centesimal composition: | |
|---|---|
| C % | 32.03 |
| H % | 3.23 |
| N % | 18.68 |
| Li % | 3.70 |

EXAMPLE 7

Activity of the manganese derivative of guanylic acid

To demonstrate the advantage of this product, synthesised in example 2, various studies have been conducted in animal and man.

1) Animal studies

In respect of acute toxicity, the LD 50 by oral route in mice and rats was found to be higher than 5 g/kg. This toxicity is therefore very low. With repeated administrations for two weeks in rats at a dose of 1 g/kg/d no change in behavioural and biological parameters was observed.

From a pharmacological viewpoint, anti-asthenia activity was evidenced in rats kept under normobar hypoxia as described by Prioux-Guyonneau et al. (J. Physiol, 1976, 72, 579–587). This hypoxia leads to reduced motility and exploratory activity which is restored by a single administration of 0.1 g/kg of the test derivative one hour before the test.

Partial magnesium deficiency (40 ppm/d) induced as described by Durlach et al. (In Magnesium Deficiency: Physiopathology and Treatment Implications, Edit. Halpern, Durlach and Kargeras 1984) causes behavioural disorders, in particular reduced learning capacity seen during sound avoidance behaviour (Pole Climbing Test). A two-week treatment by oral route with the derivative at a dose of 100 mg/kg/d overcomes the effects of this deficiency on behavioural disorders.

2. Studies in man

A clinical study, conducted in five patients aged over 70 years who complained of memory disorders together with considerable intellectual fatigue, which used a daily dose of 300 mg of the derivative in the form of gastro-resistant film-coated tablets, showed an improvement in various symptoms and recovery of normal cognitive activity in these patients.

No side effect was observed in these patients.

We claim:

1. Guanylic acid derivatives according to either of the following general formulae (I) and (II):

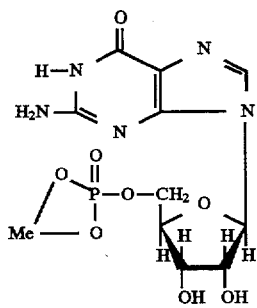

(I)

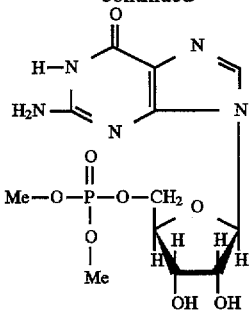

(II)

in which Me is a metal trace element involved in the enzymatic activity of physiological processes.

2. The derivatives in accordance with claim 1, characterized in that Me is a metal able to form a monovalent or divalent cation.

3. The derivatives in accordance with claim 1, characterized in that Me is Mg, Cu, Ca, Co, Zn, Ni, Se, Mn, Li or Fe.

4. The derivatives in accordance with claim 1, characterized in that they are in the form of racemic mixtures or in the form of stereoisomers.

5. A drug containing at least one of the compounds in accordance with claim 1.

6. The drug in accordance with claim 5, characterized in that it comprises a quantity of active derivative that is adapted to a daily dosage in man of between 0.2 and 3 g.

7. A pharmaceutical composition containing an effective quantity of at least one derivative of claim 1, in association with one or more diluents, excipients or additives that are compatible and pharmaceutically acceptable.

8. The pharmaceutical composition in accordance with claim 8 prepared for oral, parenteral or intravenous administration.

9. A method of treating psychasthenia, depression, anxiety, cerebral asthenia, vascular illnesses or cation deficiencies, comprising administering the guanylic acid derivative of claim 1 to a patient in need thereof.

10. A method of treating psychasthenia or depression comprising:

administering the guanylic acid derivative of claim 1 to a patient in need thereof.

* * * * *